US012690891B2

(12) United States Patent
Oikawa et al.

(10) Patent No.: US 12,690,891 B2
(45) Date of Patent: Jul. 28, 2026

(54) ROD FOR SPINAL BRACE

(71) Applicant: GLOBERIDE, Inc., Higashikurume (JP)

(72) Inventors: Katsuhiro Oikawa, Higashikurume (JP); Takuji Kawamura, Higashikurume (JP)

(73) Assignee: GLOBERIDE, Inc., Tokyo (JP)

( * ) Notice: Subject to any disclaimer, the term of this patent is extended or adjusted under 35 U.S.C. 154(b) by 74 days.

(21) Appl. No.: 18/566,193

(22) PCT Filed: Mar. 3, 2022

(86) PCT No.: PCT/JP2022/009087
§ 371 (c)(1),
(2) Date: Dec. 1, 2023

(87) PCT Pub. No.: WO2023/013127
PCT Pub. Date: Feb. 9, 2023

(65) Prior Publication Data
US 2024/0252211 A1　　Aug. 1, 2024

(30) Foreign Application Priority Data

Aug. 5, 2021　(JP) ................................. 2021-129232

(51) Int. Cl.
*A61B 17/70*　　　(2006.01)
*A61L 31/12*　　　(2006.01)
*A61L 31/14*　　　(2006.01)

(52) U.S. Cl.
CPC .......... *A61B 17/7002* (2013.01); *A61L 31/12* (2013.01); *A61L 31/14* (2013.01)

(58) Field of Classification Search
CPC ................................... A61B 17/7002–17/7013
See application file for complete search history.

(56) References Cited

U.S. PATENT DOCUMENTS 5,556,687 A　*　9/1996　McMillin ........... A61B 17/7007
87/8
2005/0228388 A1　10/2005　Brodke et al.
(Continued)

FOREIGN PATENT DOCUMENTS

JP　　2007-530216 A　　11/2007
JP　　2009-524496 A　　7/2009
(Continued)

OTHER PUBLICATIONS

Nov. 14, 2024 Extended European Search Report issued in European Patent Application No. 22852556.4.
(Continued)

*Primary Examiner* — Julianna N Harvey
(74) *Attorney, Agent, or Firm* — Oliff PLC

(57) ABSTRACT

A fixture rod includes a plurality of layers of a reinforcing fiber layer and a plurality of layers of any one of a resin layer, a reinforcing fiber layer having fibers different from those of the reinforcing fiber layer, and a reinforcing fiber layer having fibers obliquely oriented with respect to a fiber direction of the reinforcing fiber layer, in which the plurality of layers are each alternately formed as viewed in a cross-section. The fixture rod reduces damage at the time of fixing with a screw, has high rigidity and high durability against a deformation load, and has greatly improved safety even at the time of breaking.

15 Claims, 2 Drawing Sheets

(56) References Cited

U.S. PATENT DOCUMENTS

| | | | | |
|---|---|---|---|---|
| 2006/0189982 | A1* | 8/2006 | Lange | A61B 17/701 |
| | | | | 606/301 |
| 2006/0247638 | A1* | 11/2006 | Trieu | A61B 17/7031 |
| | | | | 606/907 |
| 2007/0078461 | A1* | 4/2007 | Shluzas | A61B 17/7044 |
| | | | | 606/279 |
| 2007/0191840 | A1 | 8/2007 | Pond et al. | |
| 2007/0233073 | A1* | 10/2007 | Wisnewski | A61B 17/7019 |
| | | | | 606/250 |
| 2007/0243368 | A1* | 10/2007 | Edwards | B32B 1/08 |
| | | | | 428/297.4 |
| 2008/0015578 | A1* | 1/2008 | Erickson | A61L 31/16 |
| | | | | 606/281 |
| 2008/0262548 | A1* | 10/2008 | Lange | A61B 17/7037 |
| | | | | 606/264 |
| 2008/0319486 | A1* | 12/2008 | Hestad | A61B 17/7031 |
| | | | | 606/255 |
| 2009/0093819 | A1* | 4/2009 | Joshi | A61B 17/7004 |
| | | | | 606/103 |
| 2009/0163955 | A1 | 6/2009 | Moumene et al. | |
| 2011/0106162 | A1* | 5/2011 | Ballard | A61B 17/701 |
| | | | | 606/279 |
| 2011/0172715 | A1 | 7/2011 | Pond, Jr. et al. | |
| 2012/0029564 | A1* | 2/2012 | Trieu | A61B 17/7029 |
| | | | | 29/447 |
| 2012/0071928 | A1 | 3/2012 | Jackson | |
| 2014/0257394 | A9 | 9/2014 | Jackson | |
| 2015/0366588 | A9 | 12/2015 | Jackson | |
| 2016/0346010 | A1 | 12/2016 | Jackson | |
| 2017/0246356 | A1 | 8/2017 | Preiss-Bloom et al. | |
| 2019/0183534 | A1 | 6/2019 | Jackson | |
| 2021/0205505 | A1 | 7/2021 | Preiss-Bloom et al. | |
| 2021/0251666 | A1 | 8/2021 | Jackson | |

FOREIGN PATENT DOCUMENTS

| | | |
|---|---|---|
| JP | 2011-508623 A | 3/2011 |
| JP | 2013540468 A | 11/2013 |
| JP | 2017-538483 A | 12/2017 |

OTHER PUBLICATIONS

Feb. 6, 2024 International Preliminary Report on Patentability issued in International Patent Application No. PCT/JP2022/009087.

May 24, 2022 Search Report issued in International Patent Application No. PCT/JP2022/009087.

May 28, 2024, Office Action issued in Japanese Patent Application No. 2021-129232.

Oct. 8, 2024 Office Action issued in Japanese Patent Application No. 2021-129232.

* cited by examiner

ROD FOR SPINAL BRACE

CROSS REFERENCE

The present application claims priority based on Japanese Patent Application No. 2021-129232 (filed on Aug. 5, 2021), the contents of which are incorporated herein by reference in their entirety.

TECHNICAL FIELD

The present invention relates to a fixture rod used for a fixture for fixing the spine.

BACKGROUND ART

Conventionally, fixture rods using metal have been known as fixtures for fixing the spine.

As such a fixture rod, for example, Patent Literature 1 discloses a spinal pedicle rod including an internally reinforced polymer core at least partially encased in a polymer coating.

CITATION LIST

Patent Literature

Patent Literature 1: JP 2011-508623 A

SUMMARY OF INVENTION

Technical Problem

A fixture rod using metal is generally excellent in terms of fixing force and strength but has a problem that a magnetic field is affected by magnetization of the metal in the magnetic field at the time of imaging by MRI or the like, image disturbance occurs, and diagnosis based on a captured image is difficult. On the other hand, with the rod disclosed in Patent Literature 1, although there is no such problem, it has been found that it is difficult to impart desired rigidity because the fiber density is lowered, and not only it is less likely to obtain strength and durability, but also there is a problem in safety because spinate fibers are exposed at the time of breaking.

One object of the present invention is to provide a fixture rod that reduces damage at the time of fixing with a screw, has high rigidity and high durability against a deformation load, and has greatly improved safety even at the time of breaking. Objects of the present invention other than these will be become apparent by referring to the overall description disclosed herein.

Solution to Problem

A fixture rod according to one embodiment of the present invention comprises a plurality of layers of a reinforcing fiber layer and a plurality of layers of any one of a resin layer, a reinforcing fiber layer having fibers different from those of the reinforcing fiber layer, and a reinforcing fiber layer having fibers obliquely oriented with respect to a fiber direction of the reinforcing fiber layer, in which the plurality of layers are each alternately formed as viewed in a cross-section.

With regard to the fixture rod according to one embodiment of the present invention, the reinforcing fiber layer is a fiber-reinforced resin, in which carbon, glass, boron, SiC, or aramid is used as fibers, and epoxy, phenol, unsaturated polyester, PA, PC, PPSU, POM, PP, PE, ABS, PS, PAEK, or PEEK is used as a resin.

With regard to the fixture rod according to one embodiment of the present invention, a resin of the resin layer is epoxy, phenol, unsaturated polyester, PA, PC, PPSU, POM, PP, PE, ABS, PS, PAEK, or PEEK.

With regard to the fixture rod according to one embodiment of the present invention, the reinforcing fiber layer having fibers different from those of the reinforcing fiber layer is a fiber-reinforced resin, in which carbon, glass, boron, SiC, or aramid is used as fibers, and epoxy, phenol, unsaturated polyester, PA, PC, PPSU, POM, PP, PE, ABS, PS, PAEK, or PEEK is used as a resin.

With regard to the fixture rod according to one embodiment of the present invention, in the reinforcing fiber layer or the reinforcing fiber layer having fibers different from those of the reinforcing fiber layer, fibers are aligned in one direction, formed in a woven fabric form, or randomly oriented. Furthermore, with regard to the fixture rod according to one embodiment of the present invention, a fiber direction of the reinforcing fiber layer having fibers obliquely oriented with respect to the fiber direction of the reinforcing fiber layer is obliquely oriented in the range of $10°$ to $90°$.

With regard to the fixture rod according to one embodiment of the present invention, when a plurality of layers of any one of a resin layer, a reinforcing fiber layer having fibers different from those of the reinforcing fiber layer, and a reinforcing fiber layer having fibers obliquely oriented with respect to the fiber direction of the reinforcing fiber layer are provided, the layers are the same layers or different layers.

With regard to the fixture rod according to one embodiment of the present invention, the fibers of the reinforcing fiber layer are long fibers.

With regard to the fixture rod according to one embodiment of the present invention, a fiber content of the reinforcing fiber layer is 60 weight % or more.

With regard to the fixture rod according to one embodiment of the present invention, fiber directions of the reinforcing fiber layers are aligned, and thicknesses of the layers are in a range of 0.02 mm to 0.25 mm.

Advantageous Effects of Invention

According to each of the above-described embodiments of the present invention, it is possible to provide a fixture rod that reduces damage at the time of fixing with a screw, has high rigidity and high durability against a deformation load, and has greatly improved safety even at the time of breaking.

DESCRIPTION OF EMBODIMENTS

Hereinafter, embodiments of a fixture rod according to the present invention will be specifically described with reference to the accompanying drawings. Constituent elements common in a plurality of drawings are assigned with the same reference signs throughout the plurality of drawings. It should be noted that each of the drawings are not necessarily drawn to scale for convenience of description.

Figure 1:
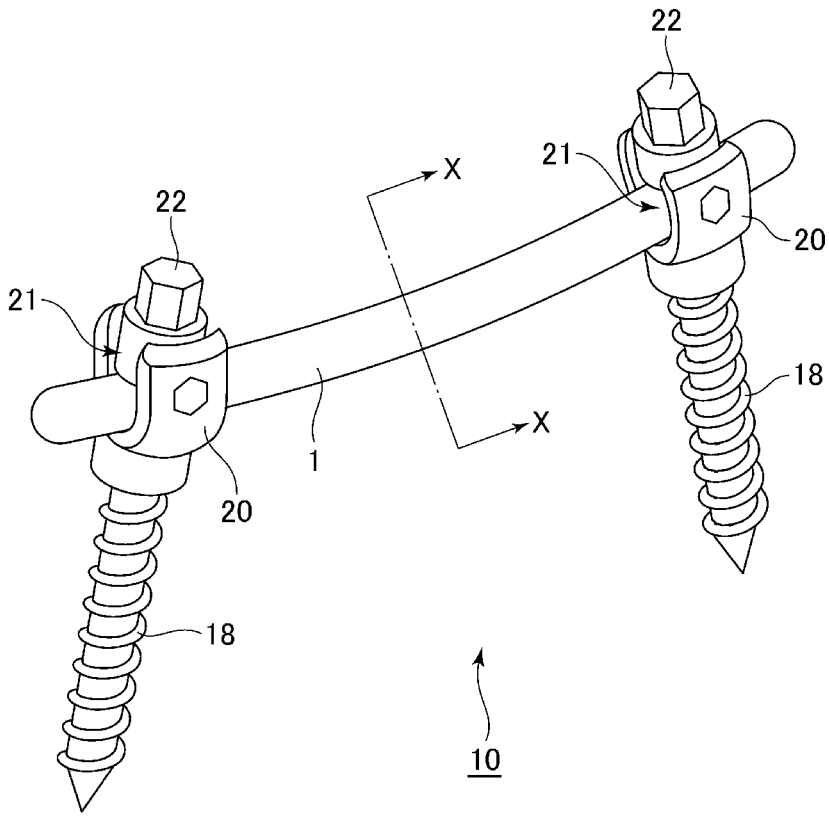
FIG. 1 is a view illustrating a spinal fixture 10 comprising a fixture rod according to one embodiment of the present invention.

FIG. 1 is a view illustrating a spinal fixture 10 comprising a fixture rod 1 according to one embodiment of the present invention. As shown in the drawing, the spinal fixture 10 comprises: a plurality of screw members 18 (two screw members 18 in the example shown in the drawing) to be fixed to the bone of the spine; a plurality of rod fixing members 20 (two rod fixing members 20 in the example shown in the drawing) to be attached to the screw members 18, each comprising a recess 21 for receiving the fixture rod and a pressing member 22; and a fixture rod 1 to be inserted into the recess 21 of the plurality of rod fixing members 20 and fixed by the pressing member 22.

Figure 2:
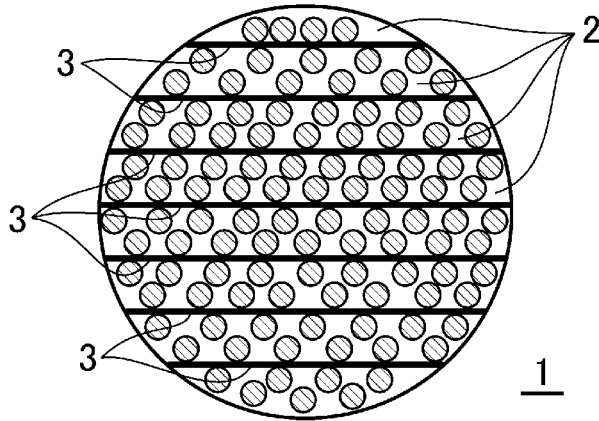
FIG. 2 is a view schematically illustrating a cross-section of the fixture rod according to one embodiment of the present invention taken along a plane perpendicular to a central axis of the fixture rod.
Figure 3:
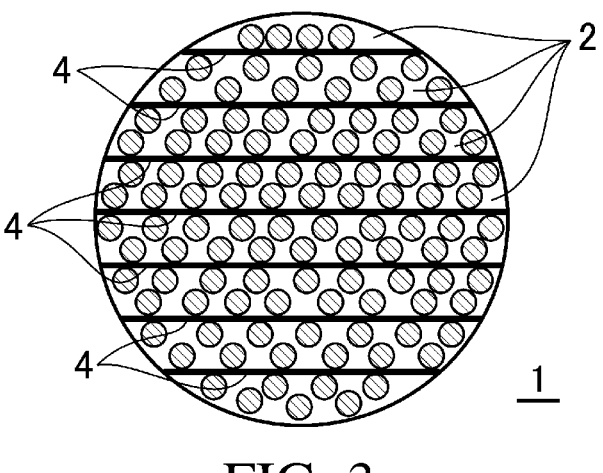
FIG. 3 is a view schematically illustrating a cross-section of the fixture rod according to one embodiment of the present invention taken along a plane perpendicular to a central axis of the fixture rod.
Figure 4:
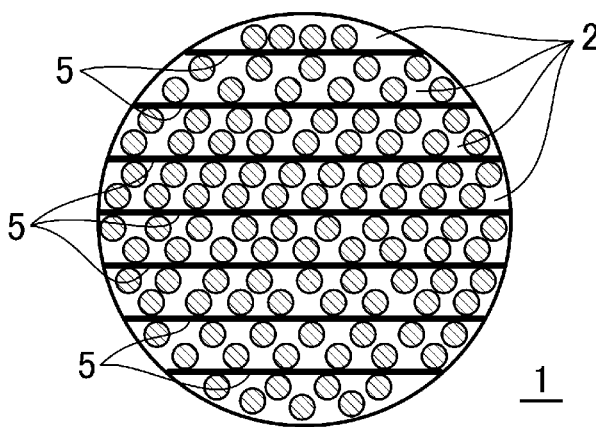
FIG. 4 is a view schematically illustrating a cross-section of the fixture rod according to one embodiment of the present invention taken along a plane perpendicular to a central axis of the fixture rod.

Next, the fixture rod 1 according to one embodiment of the present invention, which is used for the spinal fixture 10, will be described with reference to FIGS. 2, 3, and 4. FIGS. 2, 3, and 4 show the fixture rod 1 shown in FIG. 1 as viewed in a cross-section taken along line X-X shown in FIG. 1. In the fixture rod 1 according to one embodiment of the present invention, a plurality of layers of a reinforcing fiber layer 2 and a plurality of layers of any one of a resin layer 3 (example shown in FIG. 2), a reinforcing fiber layer 4 having fibers different from those of the reinforcing fiber layer (example shown in FIG. 3), and a reinforcing fiber layer 5 having fibers obliquely oriented with respect to a fiber direction of the reinforcing fiber layer (example shown in FIG. 4), are each alternately formed as viewed in a cross-section. Here, the reinforcing fiber layer 2 and any one of the resin layer 3 (example shown in FIG. 2), the reinforcing fiber layer 4 having fibers different from those of the reinforcing fiber layer (example shown in FIG. 3), and the reinforcing fiber layer 5 having fibers obliquely oriented with respect to the fiber direction of the reinforcing fiber layer (example shown in FIG. 4) are formed to have a thickness of 0.01 mm to 0.25 mm; however, the thickness of the layers may vary depending on the location in a layer (that is, the layers may be formed such that there may be portions with small thicknesses and portions with large thicknesses). The layers may be formed intermittently (that is, not only there may be portions with small thicknesses as well as portions with large thicknesses, but also portions where the thickness of the layer is 0 may be intercalated).

With the fixture rod 1 according to one embodiment of the present invention, it is possible to provide a fixture rod that reduces damage at the time of fixing with a screw, has high rigidity and high durability against a deformation load, and has greatly improved safety even at the time of breaking. Particularly, it has been found that at the time of breaking of the fixture rod 1 according to one embodiment of the present invention, by concentrating stress on any one of the resin layer, the reinforcing fiber layer having fibers different from those of the reinforcing fiber layer, and the reinforcing fiber layer having fibers obliquely oriented with respect to the fiber direction of the reinforcing fiber layer, which are sandwiched between the reinforcing fiber layers, the chance of the reinforcing fiber layer becoming spinate when the rod is broken is reduced, and as a result, it is possible to significantly enhance the safety to the human body.

With regard to the fixture rod 1 according to one embodiment of the present invention, the reinforcing fiber layer 2 is a fiber-reinforced resin, in which carbon, glass, boron, SiC, or aramid is used as fibers, and epoxy, phenol, unsaturated polyester, PA, PC, PPSU, POM, PP, PE, ABS, PS, PAEK, or PEEK is used as a resin. In this way, it is possible to increase the bending rigidity and the strength of the fixture rod 1.

With regard to the fixture rod 1 according to one embodiment of the present invention, the resin of the resin layer 3 is epoxy, phenol, unsaturated polyester, PA, PC, PPSU, POM, PP, PE, ABS, PS, PAEK, or PEEK.

With regard to the fixture rod according to one embodiment of the present invention, the reinforcing fiber layer 4 having fibers different from those of the reinforcing fiber layer 2 is a fiber-reinforced resin, in which carbon, glass, boron, SiC, or aramid is used as fibers, and epoxy, phenol, unsaturated polyester, PA, PC, PPSU, POM, PP, PE, ABS, PS, PAEK, or PEEK is used as a resin. In this way, it is possible to increase the bending rigidity and the strength of the fixture rod. The reason for using a reinforcing fiber layer having fibers different from those of the reinforcing fiber layer is that different characteristics such as flexibility and vibration absorbing properties other than rigidity and strength can be imparted by using different materials.

With regard to the fixture rod according to one embodiment of the present invention, in the reinforcing fiber layer or the reinforcing fiber layer having fibers different from those of the reinforcing fiber layer, the fibers may be aligned in one direction, formed in a woven fabric form, or randomly oriented. Furthermore, with regard to the fixture rod 1 according to one embodiment of the present invention, the fiber direction of the reinforcing fiber layer 5 having fibers obliquely oriented with respect to the fiber direction of the reinforcing fiber layer 2 may be obliquely oriented in the range of 10° to 90°. In this way, it is possible to realize intended strength and rigidity by arranging an appropriate laminated configuration.

With regard to the fixture rod 1 according to one embodiment of the present invention, when a plurality of layers of any one of the resin layer 3, the reinforcing fiber layer 4 having fibers different from those of the reinforcing fiber layer, and the reinforcing fiber layer 5 having fibers obliquely oriented with respect to the fiber direction of the reinforcing fiber layer are provided, the layers are the same layers or different layers (hereinafter, the same applies). In this regard, for example, when two layers are provided, two layers of the resin layer 3 may be provided (in this case, each layer is the same), or two different layers such as the resin layer 3 and the reinforcing fiber layer 4 having fibers different from those of the reinforcing fiber layer, may be provided. In the case of providing three or more layers, a desired combination may be selected and provided from among the above-described layers. In this way, intended strength and rigidity can be realized by arranging an appropriate laminated configuration.

With regard to the fixture rod 1 according to one embodiment of the present invention, it is configured such that the fibers of the reinforcing fiber layer 3 are long fibers. In this way, when the fibers of the reinforcing fiber layer 3 are long fibers, it is possible to further increase the bending rigidity and the strength.

Furthermore, with regard to the fixture rod 1 according to one embodiment of the present invention, it is configured such that the fiber content of the reinforcing fiber layer 3 is 60 weight % or more. In this way, it is possible to form a fixture rod 1 having high rigidity and excellent durability due to fiber layers in which long fibers are focused at high density.

With regard to the fixture rod 1 according to one embodiment of the present invention, the fiber directions of the reinforcing fiber layers are aligned, and thicknesses of the layers are, for example, in the range of 0.02 mm to 0.25 mm. In this way, the density of the resin is made uniform, and it is possible to reduce the variation in strength depending on sites.

Next, a method for manufacturing the fixture rod 1 according to one embodiment of the present invention will be described. First, as step 1, the reinforcing fiber layer 2, and any one of the resin layer 3, the reinforcing fiber layer 4 having fibers different from those of the reinforcing fiber layer, and the reinforcing fiber layer 5 having fibers obliquely oriented with respect to the fiber direction of the reinforcing fiber layer is cut to predetermined dimensions (layer cutting step). Then, as step 2, each layer is laminated in a predetermined arrangement (layer lamination process). As step 3, the lamination product is placed in a predetermined mold and molded under predetermined conditions (for example, the temperature is 140° C., and the pressure is 0.1 to 0.5 MPa) (molding step). Next, as step 4, the molded product is subjected to processing into a final shape and dimensions (processing step). In this way, the fixture rod 1 according to one embodiment of the present invention is formed.

With the fixture rod 1 according to one embodiment of the present invention formed in this manner, it is possible to provide a fixture rod that reduces damage at the time of fixing with a screw, has high rigidity and high durability against a deformation load, and has greatly improved safety even at the time of breaking. Particularly, it has been found that at the time of breaking of the fixture rod 1 according to one embodiment of the present invention, by concentrating stress on any one of the resin layer, the reinforcing fiber layer having fibers different from those of the reinforcing fiber layer, and the reinforcing fiber layer having fibers obliquely oriented with respect to the fiber direction of the reinforcing fiber layer, which are sandwiched between the reinforcing fiber layers, the chance of the reinforcing fiber layer becoming spinate when the rod is broken is reduced, and as a result, it is possible to significantly enhance the safety to the human body.

Figure 5:
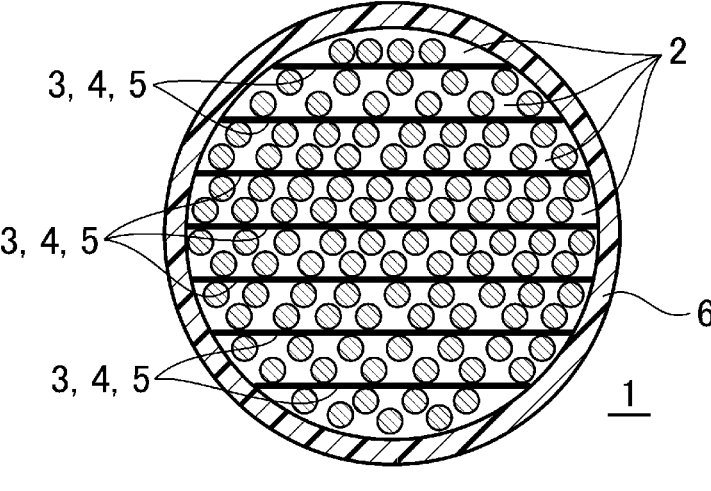
FIG. 5 is a view schematically illustrating a cross-section of the fixture rod according to one embodiment of the present invention taken along a plane perpendicular to a central axis of the fixture rod.

Finally, a fixture rod 1 according to another embodiment of the present invention, which is used for the spinal fixture 10, will be described with reference to FIG. 5. FIG. 5 illustrates the fixture rod 1 shown in FIG. 1 as viewed in a cross-section taken along line X-X shown in the same drawing. In a fixture rod 1 according to one embodiment of the present invention, a plurality of layers of a reinforcing fiber layer 2 and a plurality of layers of any one of a resin layer 3, a reinforcing fiber layer 4 having fibers different from those of the reinforcing fiber layer, and a reinforcing fiber layer 5 having fibers obliquely oriented with respect to a fiber direction of the reinforcing fiber layer, are each alternately formed as viewed in a cross-section, and a cover layer 6 is further formed on an outer surface of the fixture rod 1. The cover layer 6 may be considered, for example, to be the same as the resin of the layers used in the above-described fixture rod 1; however, the cover layer 6 is not limited thereto. In this way, the chance of the reinforcing fiber layer becoming spinate when the rod is broken is further reduced, and as a result, it is possible to further enhance the safety to the human body.

Dimensions, materials, and arrangements of the constituent elements described in the present specification are not limited to those explicitly described in the embodiments, and these constituent elements may be reshaped to have any dimensions, materials, and arrangements that may fall within the scope of the present invention. Furthermore, any constituent elements that are not explicitly described in the present specification can be added to the described embodiments, or some of the constituent elements described in each embodiment can be omitted.

REFERENCE SIGNS LIST

1 Fixture rod
2 Reinforcing fiber layer
3 Resin layer
4 Reinforcing fiber layer having fibers different from those of reinforcing fiber layer
5 Reinforcing fiber layer having fibers obliquely oriented with respect to fiber direction of reinforcing fiber layer
6 Cover layer
10 Spinal fixture
18 Screw member
20 Rod fixing member
21 Recess
22 Pressing member

The invention claimed is:

1. A fixture rod comprising:
a first plurality of layers including reinforcing fiber layers and a second plurality of layers including resin layers, the reinforcing fiber layers being thicker than the resin layers; and
a cover layer acting as an outer surface of the fixture rod and covering at least a portion of the first plurality of layers and the second plurality of layers, wherein
each of the first plurality of layers is alternately formed with each of the second plurality of layers so as to be stacked in a direction substantially perpendicular to an axial direction of the fixture rod as viewed in a cross-section taken along a plane perpendicular to a central axis of the fixture rod.

2. The fixture rod according to claim 1, wherein each of the reinforcing fiber layers is a fiber-reinforced resin, in which carbon, glass, boron, SiC, or aramid is used as fibers, and epoxy, phenol, unsaturated polyester, PA, PC, PPSU, POM, PP, PE, ABS, PS, PAEK, or PEEK is used as a resin.

3. The fixture rod according to claim 1, wherein a resin of each of the resin layers is epoxy, phenol, unsaturated polyester, PA, PC, PPSU, POM, PP, PE, ABS, PS, PAEK, or PEEK.

4. The fixture rod according to claim 1, wherein the second plurality of layers further includes a reinforcing fiber layer having fibers different from those of the reinforcing fiber layers, and comprise a fiber-reinforced resin, in which carbon, glass, boron, SiC, or aramid is used as fibers, and epoxy, phenol, unsaturated polyester, PA, PC, PPSU, POM, PP, PE, ABS, PS, PAEK, or PEEK is used as a resin.

5. The fixture rod according to claim 1, wherein in the reinforcing fiber layers, fibers are aligned in one direction, formed in a woven fabric form, or randomly oriented.

6. The fixture rod according to claim 1, wherein the second plurality of layers further includes a reinforcing fiber layer having fibers obliquely oriented with respect to the fiber direction of the reinforcing fiber layers at an angle in a range of 10° to 90°.

7. The fixture rod according to claim 1, wherein fibers of the reinforcing fiber layers are long fibers.

8. The fixture rod according to claim 1, wherein a fiber content of the reinforcing fiber layers is 60 weight % or more.

9. The fixture rod according to claim 1, wherein fiber directions of the reinforcing fiber layers are aligned, and thicknesses of the reinforcing fiber layers are in a range of 0.02 mm to 0.25 mm.

10. The fixture rod according to claim 1, wherein each of the first plurality of layers and each of the second plurality of layers has a thickness dimension that extends in the direction substantially perpendicular to the axial direction of the fixture rod.

11. The fixture rod according to claim 10, wherein each of the first plurality of layers and each of the second plurality of layers has a width dimension that extends in another direction that is also substantially perpendicular to an axial direction of the fixture rod.

12. The fixture rod according to claim 1, wherein the fixture rod is rigid.

13. The fixture rod according to claim 1, wherein the cover layer forms an outer surface of the fixture rod and surrounds the first plurality of layers and the second plurality of layers as viewed in the cross-section of the fixture rod.

14. The fixture rod according to claim 1, wherein the cover layer includes a resin.

15. The fixture rod according to claim 1, wherein the reinforcing fiber layers each have fibers that are either randomly oriented or all aligned in substantially the same direction.

\* \* \* \* \*